United States Patent [19]

Tomita et al.

[11] 4,171,455

[45] Oct. 16, 1979

[54] POLYOXYPROPYLENE POLYOXYETHYLENE ADDITION ETHER OF HIGHER BRANCHED PRIMARY SATURATED ALCOHOL

[75] Inventors: Kenichi Tomita, Tokyo; Keiichi Uehara, Yokohama; Kenji Torii; Takahiro Okuda, both of Tokyo; Hakuji Katsura; Isao Hirano, both of Yokohama, all of Japan

[73] Assignee: Shiseido Company Ltd., Tokyo, Japan

[21] Appl. No.: 943,727

[22] Filed: Sep. 19, 1978

[51] Int. Cl.$^2$ .................... C07C 43/04; C07C 41/02
[52] U.S. Cl. .................... 568/625; 424/70; 424/342; 252/351; 252/358; 252/522; 252/352
[58] Field of Search .................... 568/625, 622

[56] References Cited

U.S. PATENT DOCUMENTS

| | | | |
|---|---|---|---|
| 3,185,562 | 5/1965 | Scoles et al. | 568/625 |
| 3,931,271 | 1/1976 | Baumann et al. | 568/625 |

*Primary Examiner*—Howard T. Mars
*Attorney, Agent, or Firm*—Burgess, Ryan and Wayne

[57] ABSTRACT

A novel nonionic compound, a polyoxypropylene polyoxyethylene addition ether of a higher branched primary saturated alcohol is provided. This nonionic compound is suitable for use, as a solubilizing agent, in a high concentration solution of a lower alcohol in water, for example, in cosmetics such as a transparent liquid hair preparation, a hair cologne, an after-shaving lotion, a skin lotion and the like.

4 Claims, 4 Drawing Figures

POLYOXYPROPYLENE POLYOXYETHYLENE ADDITION ETHER OF HIGHER BRANCHED PRIMARY SATURATED ALCOHOL

BACKGROUND OF THE INVENTION

1. Field of the Invention

The present invention relates to novel nonionic compounds, polyoxypropylene polyoxyethylene addition ethers of a higher branched primary saturated alcohol suitable for use, as a solubilizing agent, in a high concentration (e.g. 40 through 80% by weight) solution of a lower alcohol (an alcohol having a lower molecular weight such as ethanol, isopropanol) in water.

2. Description of the Prior Art

Known ether type nonionic solubilizing agents include, for example, polyoxyethylene octylphenylether, polyoxyethylene nonylphenyl ether, polyoxyethylene oleyl alcohol ether, sorbitane monolaurate polyoxyethylene ether, sorbitane monooleate polyoxyethylene ether, polyoxyethylene hardened caster oil, polyoxyethylene polyoxypropylene cetyl alcohol ether and the like. The hydrophillic-lipophillic balance (H.L.B.) values of these known ether type nonionic solubilizing agents are generally within the range of from 12 to 18. These solubilizing agents can solubilize substances to be solubilized, such as, for example, oils, perfumes, oil-soluble chemical agents and the like into a water phase to produce clear solution in an amount similar to that of the substance to be solubilized. However, it is now required that the above-mentioned substances be clearly solubilized into a high concentration solution of a lower alcohol (e.g. ethyl alcohol, isopropanol or the like) in water. Although said known solubilizing agents can effectively solubilize the substances to be solubilized into a water phase, they are not necessarily effective in the case where the water phase contains a substantial amount of a lower alcohol such as ethyl alcohol, isopropanol or the like. Especially, in the case where the above-mentioned substances are solubilized into, for example, 55% by weight or more of ethyl alcohol in water solution, these known solubilizing agents cannot solubilize the above-mentioned substance into the solution in an amount similar to that of the substance to be solubilized even when the H.L.B. values of 12 through 18 of these known solubilizing agent are adjusted to the values of 10 through 14.

SUMMARY OF THE INVENTION

An object of the present invention is to provide novel nonionic compounds, polyoxypropylene polyoxyethylene addition ether of a higher branched primary saturated alcohol.

Another object of the present invention is to provide a solubilizing agent suitable for solubilizing substances such as oils, perfumes, water-insoluble chemical agents in 35% by weight or more of a high concentration solution of a lower alcohol in water, such as, cosmetics, medicines and the like.

Other objects and advantages of the present invention will be apparent from the following description.

In accordance with the present invention there is provided a polyoxypropylene polyoxyethylene addition ether of a higher branched primary saturated alcohol having the general formula (1),

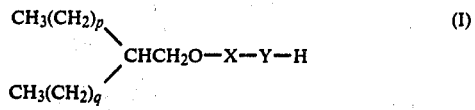

wherein P represents an integer of 7 to 19, q represents an integer of p plus two, X represents

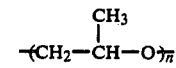

(wherein n represents an integer of 5 to 30) and Y represents $-(CH_2CH_2-O)_m-$ (wherein m represents an integer of 5 to 60).

In accordance with the present invention, there is also provided a solubilizing agent for a high concentration solution of a lower alcohol in water comprising a polyoxypropylene polyoxyethylene addition ether of a higher branched primary saturated alcohol having the above-mentioned general formula (I). The solubilizing agent of the present invention can be effectively incorporated into cosmetics such as, for example, a transparent liquid hair preparation, a hair cologne, an after-shaving lotion, a skin lotion and the like, for solubilizing substances such as oils, perfumes and water-insoluble chemical agents in a high concentration solution (e.g. 35% by weight or more) of a lower alcohol in water.

DESCRIPTION OF PREFERRED EMBODIMENT

Figure 1:
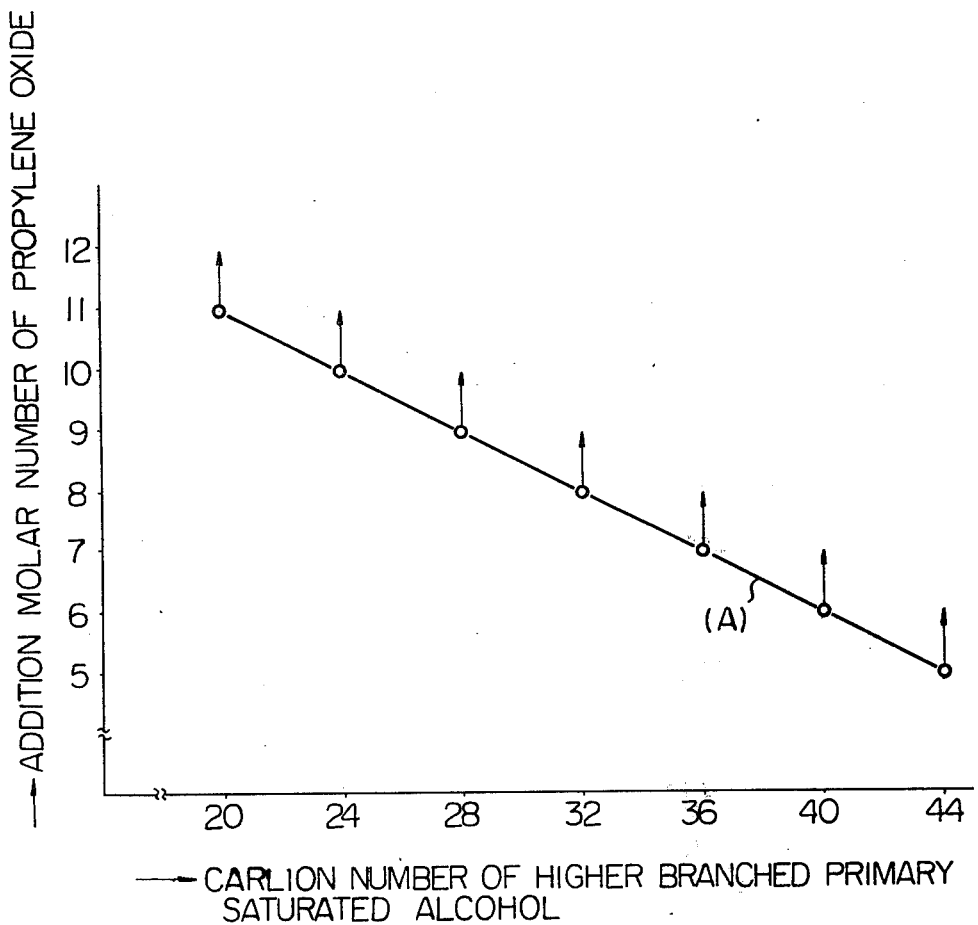

The nonionic compounds of the present invention having the general formula (I) above can be prepared by effecting addition reactions of a higher branched primary saturated alcohol with the required number of moles of propylene oxide and, subsequently, with the required number of moles of ethylene oxide. These addition reactions can be carried out in a known manner, for example, under raised temperatures and pressures in the presence of known catalysts such as alkaline metal hydroxides and alkaline metal carbonates.

The higher branched primary saturated alcohol used, as the starting material in the present invention includes, for example, those which are prepared by the dimerization reaction of linear saturated aliphatic alcohols such as, for example, decanol, dodecanol, tetradecanol, hexadecanol, octadecanol, eicosanol, docosanol and the like according to the Guerbet reaction.

The inventors of the present invention have found that the polyoxypropylene polyoxyethylene addition ether of a higher branched primary saturated alcohol having the general formula (I) can solubilize substances, such as oils, perfumes, chemical agents and the like, into a high concentration (e.g. 40 through 80% by weight) solution of a lower alcohol in water.

The solubilizing agent of the present invention can be prepared as follows. 1 mol of a higher branched primary saturated alcohol having a carbon number of 20 through 44 (for brevity's sake, it is called, for example, "$C_{20}$ through $C_{44}$ branched alcohol" hereinbelow) is reacted with 5 through 30 mol of propylene oxide to form an addition product, polyoxypropylene ether of a higher branched primary saturated alcohol. The total molecular weight of this polyoxypropylene ether compound (that is, the total molecular weight of the higher branched primary saturated alcohol moiety and the propylene oxide addition moiety) is preferably not less than 900, and more preferably, within the range of fromm 950 to 1450. When this total molecular weight is less than 900, the solubilizing capacity of the present solubilizing agent unpreferably decreases and also a long-term stability of the solubilized solution containing the present solubilizing agent becomes poor. The polypropylene oxide ether of higher branched primary saturated alcohol is reacted with 5 through 60 mol of ethylene oxide to produce a nonionic compound of polyoxypropylene polyoxyethylene addition ether of higher branched primary saturated alcohol. In order to provide outstanding solubilizing characteristics for a high concentration solution of a lower alcohol in water, a H.L.B. value of the nonionic polyoxypropylene polyoxyethylene addition ether type compound should be preferably within the range of from 8.0 to 12.0. The H.L.B. value can be adjusted according to the definition of: Prediction of Organic Compounds by a Conceptional Diagram, A. Fujita, Chem. & Pham. Bull., 163–173, 1954.

If the H.L.B. value of the nonionic polyoxypropylene polyoxyethylene addition ether type compound is less than 8.0, the solubilizing capacity of the present compound unpreferably decreases due to the fact that the compound becomes lipophillic. Contrary to this, if the H.L.B. value is more than 12.0, the solubilizing capacity of the present compound also decreases due to the fact that the compound becomes hydrophillic. The solubilizing agent of the present invention can solubilize substances, such as oils, perfumes, water-insoluble chemical agents and the like, into a high concentration (e.g. 35% by weight or more) solution of a lower alcohol in water in the same amount as or in an amount less than that of the substance to be solubilized.

The propylene oxide addition lipophillic moiety (i.e. the higher branched primary saturated alcohol moiety plus the propylene oxide addition moiety) having the molecular weight of 900 or more has 11 mol or more of propylene oxide addition moiety in the case of $C_{20}$ branched alcohol, and has 5 mol or more of propylene oxide addition moiety in the case of $C_{44}$ branched alcohol.

FIG. 1 shows the correlations between the carbon number of a higher branched primary saturated alcohol and the addition molar number of propylene oxide in the case where the propylene oxide addition lipophillic moiety having the molecular weight of 900 or more is obtained. The upward region of a line (A) in FIG. 1 provides the propylene oxide addition lipophillic moiety having the molecular weight of 900 or more.

Figure 2:
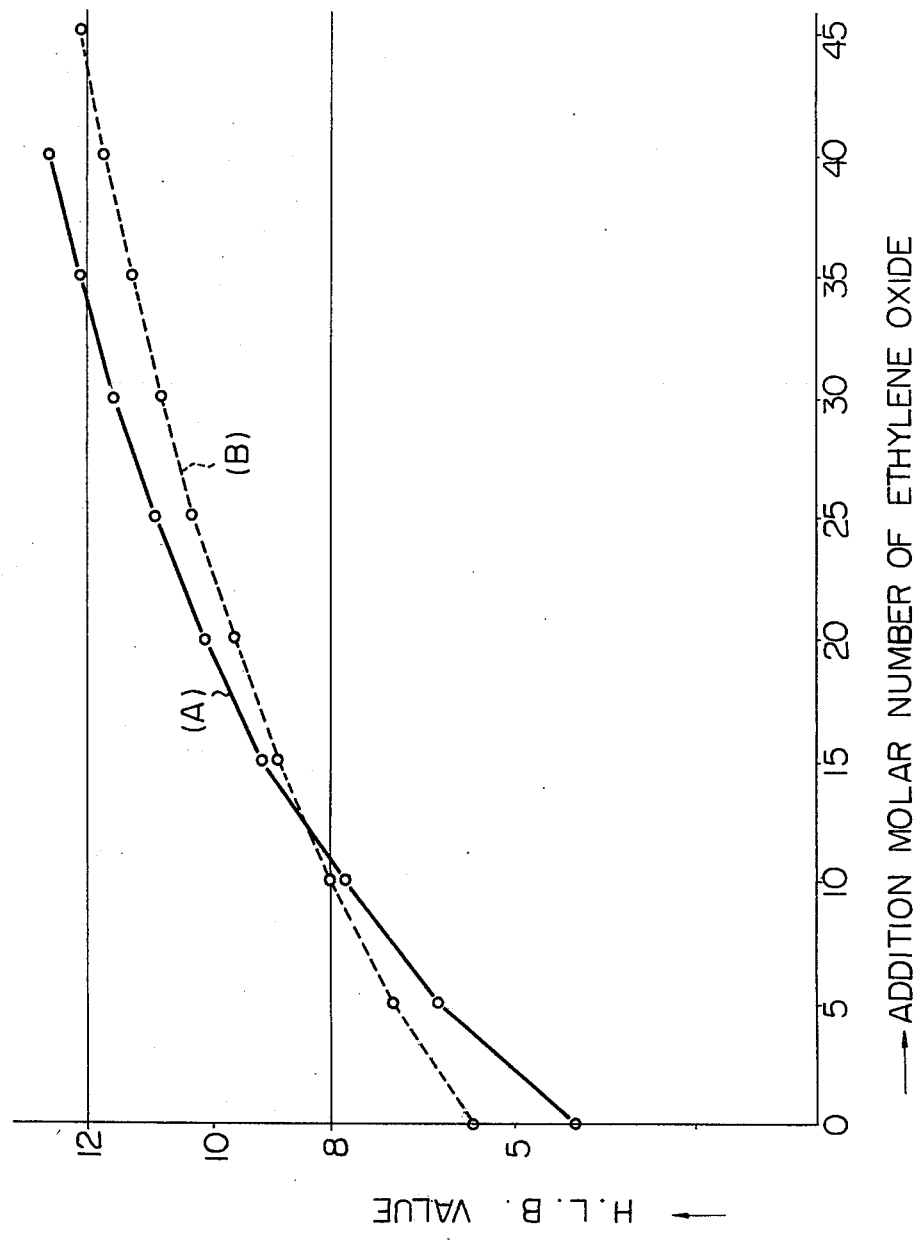

FIG. 2 shows the correlation between the H.L.B. value of the polyoxypropylene polyoxyethylene addition ether type nonionic compound of the present invention and the addition molar number of ethylene oxide in the case where the molecular weight of the propylene oxide addition lipophillic moiety is 900 or more. For example, a curve (A) of FIG. 2 represents the above-mentioned correlation in the case of the $C_{34}$ branched alcohol having 8 mol of propylene oxide addition moiety. As is apparent from the curve (A) of FIG. 2, when 11 through 35 mol of ethylene oxide are addition reacted to the $C_{34}$ branched alcohol having 8 mol of a propylene oxide addition moiety, the desired present nonionic compounds having the H.L.B. value of 8 through 12 can be obtained. A curve (B) of FIG. 2 represents the above-mentioned correlation in the case of the $C_{34}$ branched alcohol having 20 mol of a propylene oxide addition moiety. As is also clear from the curve (B) of FIG. 2, when 10 through 45 mol of ethylene oxide are addition reacted to the $C_{34}$ branched alcohol having 20 mol of a propylene oxide addition moiety, the desired present nonionic compounds having the H.L.B. value of 8 through 12 can be obtained. This correlation was determined from calculations according to the above mentioned calculation method for H.L.B. value.

The H.L.B. values of the propylene oxide addition lipophillic moieties having the molecular weight of 900 or more are varied from 2.7 (in the case of the $C_{44}$ branched alcohol having 5 mol of propylene oxide addition moiety 1 to 7.2 (in the case of the $C_{20}$ branched alcohol having 30 mol of propylene oxide addition moiety). On the other hand, H.L.B. values of the lipophillic moieties of known solubilizing agents are varied from 2.8 of oleyl alcohol to 8.3 of sorbitane monooleate. However, it should be noted that this variation can only be obtained by changing the kinds of the solubilizing agents. Further the maximum molecular weight of the lipophillic moieties of the known solubilizing agents is 932 in the case of hardened caster oil.

Figure 3:
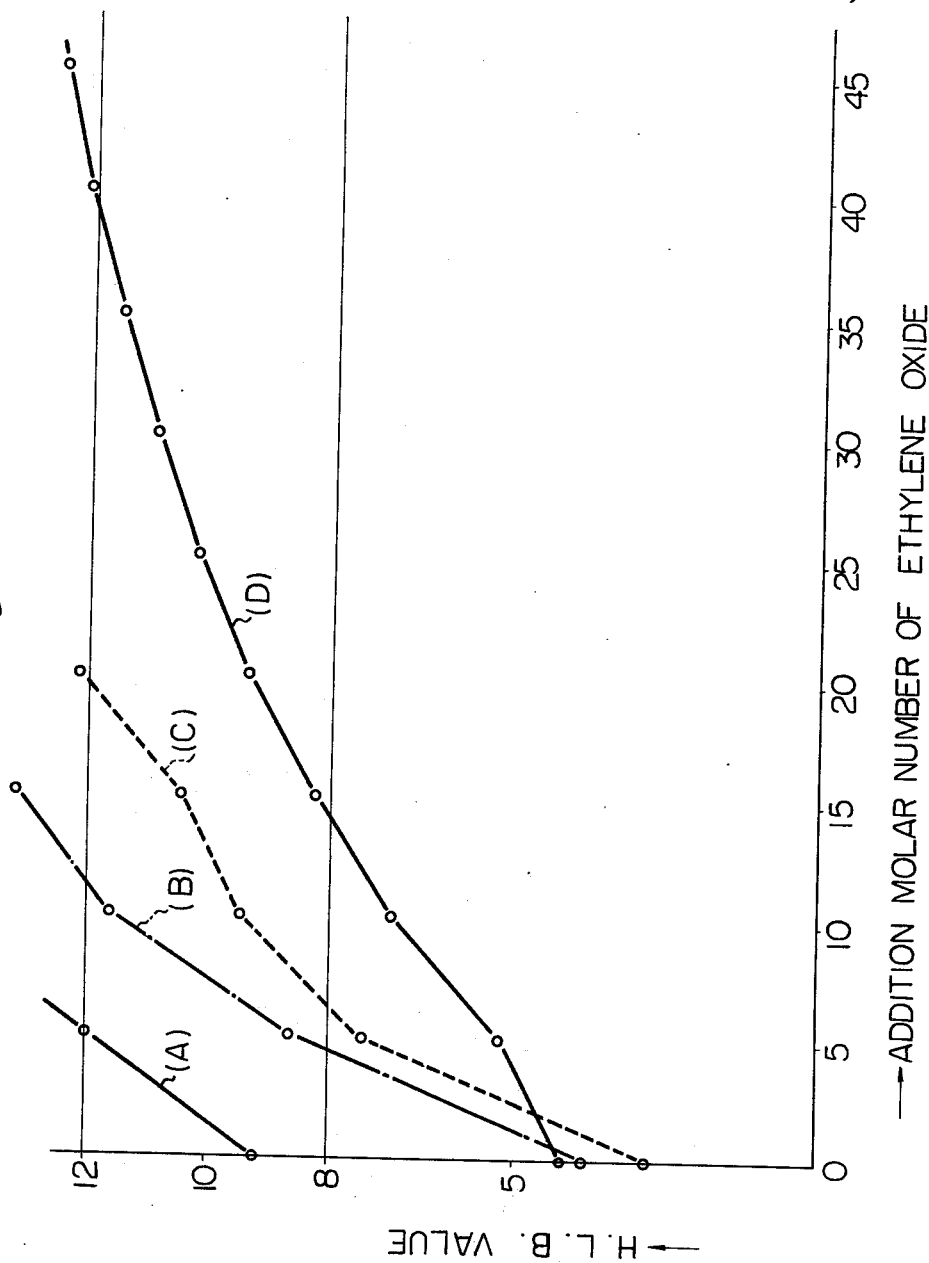
Figure 4:
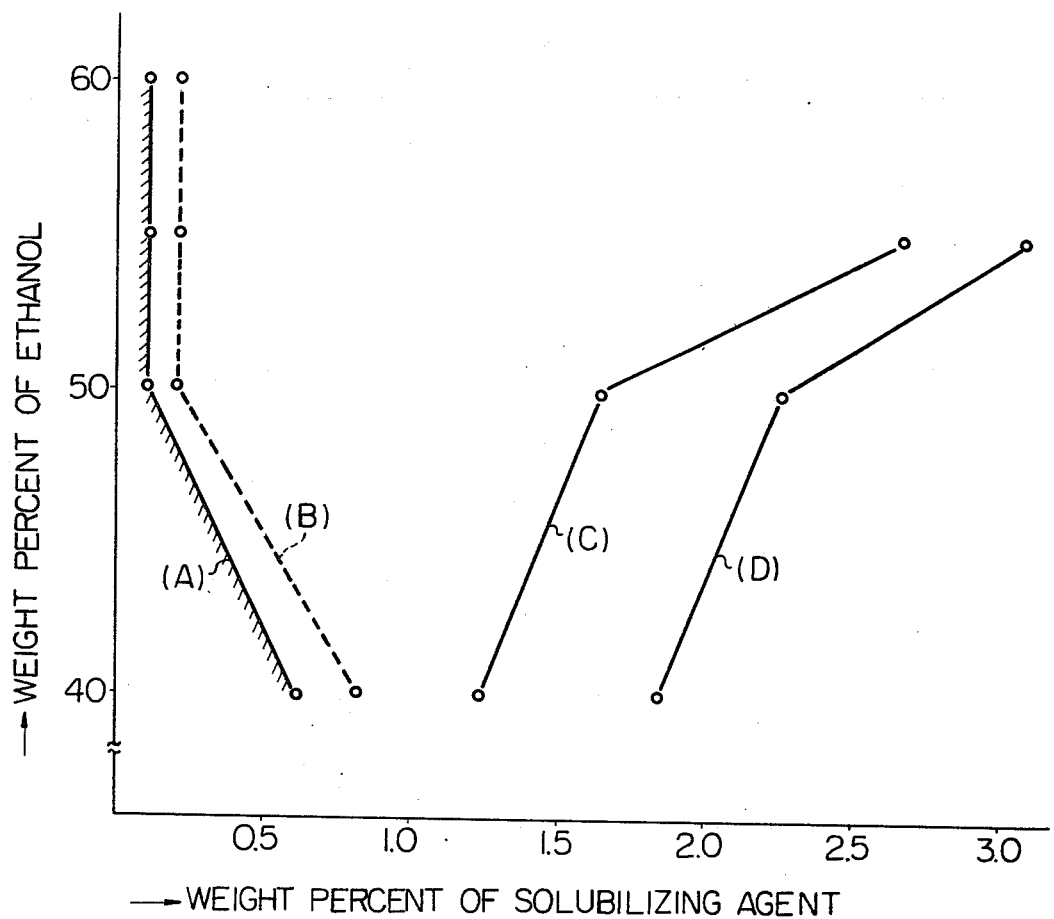

FIG. 3 shows the correlation between the H.L.B. values of the known solubilizing agents and the addition molar number of ethylene oxide. In FIG. 4, curves (A), (B), (C), and (D) represent said correlations in the case of the lipophillic moieties of sorbitane monooleate, nonyl phenol, oleyl alcohol and hardened caster oil, respectively.

The H.L.B. value and the molecular weight, of the lipophillic moiety are important factors for solubilizing substances such as oils, perfumes, chemical agents and the like, into a high concentration solution of a lower alcohol in water.

FIG. 4 shows results of solubilizing tests in which 1% by weight of a perfume having a H.L.B. value of approximately 5.3 is solubilized into 40, 50, 55 and 60% by weight of aqueous ethanol solutions by using various solubilizing agent having a H.L.B. value of 10.8. FIG. 4 shows the correlations between the weight percent of ethanol in water and the minimum weight percent of the solubilizing agent in the case where the perfume is solubilized into the aqueous ethanol solution. In FIG. 4, curves (A), (B), (C) and (D) represent said correlations in the case of the lipophillic moieties of the $C_{34}$ branched alcohol having 20 mol of propylene oxide addition product of the present invention, known hardened caster oil, known nonyl phenol and known oleyl alcohol, respectively. As is clear from FIG. 4, the solubilizing agents (A) and (B) (i.e. the present nonionic compound and the known hardened caster oil type agents, respectively) are superior to the solubilizing agents (C) and (D) (i.e. the known nonylphenol and oleyl alcohol type agents) having low molecular weights of the lipophillic moieties although the H.L.B. values of all solubilizing agents are adjusted to 10.8 that is, the solubilizing agents (A) and (B) have outstanding solubilizing characteristics in a small amount of 1.0% by weight or less. This clearly indicates the molecular weight effect of the lipophillic moiety of the solubilizing agent, that is, the solubilizing effect increases as the chain length of the lipophillic moiety of the solubilizing agent lengthens. It is believed that this effect is caused due to the fact that the number of adsorption sites fur substances to be solubilized increases in the micelle of the solubilizing agent. In addition, known solubilizing agents having sorbitane monoleate lipophillic moiety (H.L.B. value of the lipophillic moiety is 8.3) cannot solubilize perfume into 40% by weight or more of an aqueous ethanol solution, whereas the present solubilizing agent having the H.L.B. value of the lipophillic moiety of 5.3 has an outstanding solubilizing power for solubilizing perfume into a high concentration solution of ethanol in water. From this result, it should be noted that the H.L.B. value of the lipophillic moiety of the solubilizing agent is also an important factor of the solubilizing agent.

As mentioned above, according to the present invention, the solubilizing agent for solubilizing substances into a high concentration solution of a lower alcohol in water having the following advantages is provided.

(1) The H.L.B. value of the lipophillic moiety of the solubilizing agent can be freely adjusted to that of substances to be solubilized.

(2) Since the molecular weight of the lipophillic moiety of the solubilizing agent is large (900 or more), a micelle formation capacity in the high concentration solution of a lower alcohol in water is large and the number of the adsorption sites for substances to be solubilized in the micelle increases. Thus, ideal ether type nonionic solubilizing agents are provided.

The present solubilizing agent can be advantageously incorporated into cosmetics containing a high concentration of a lower alcohol for solubilizing substances such as perfumes, vitamins, hormones and the like. Example of such cosmetics are a transparent liquid hair preparation, a hair cologne, an after-shaving lotion, a skin lotion and the like. The amount of the present solubilizing agent incorporated into cosmetics can be varied depending upon the kind and amount, of substances to be solubilized, the type of cosmetics and the like. The amount of the present solubilizing agent incorporated into cosmetics is preferably within the range of from 0.1 to 7 w/w%, and more preferably from 0.5 to 1.5 w/w%.

The present invention will be further illustrated by, but is by no means limited to, the following examples together with comparative examples.

EXAMPLE 1

Synthesis of Polyoxyethylene (25) polyoxypropylene (20)-2-hexadecyl-octadecyl alcohol ether.

Into an autoclave 1 mol of 2-hexadecyl-octadecanol and, as a catalyst, 0.3% by weight of potassium hydroxide based upon the 2-hexadecyl-octadecanol were charged, and, then, after air contained within the autoclave was replaced with dry nitrogen, the mixture was heated to 150° C. under agitation to completely dissolve the catalyst. Thereafter, 20 mol of propylene oxide was dropwise added from a cooled dropping apparatus provided with a cooling means to the mixture in the autoclave and the mixture was stirred under the same conditions. After the completion of the reaction, the agitation was continued for further 35 minutes to age the reaction mixture.

After cooling, the reaction mixture was taken out of the autoclave and neutralized to a pH of 6 to 7 with phosphoric acid. In order to remove water contained in the reaction mixture thus neutralized, the reaction mixture was treated at a temperature of 100° C. under a reduced pressure of 10 mmHg for 30 minutes. Thereafter, the reaction mixture was filtered through a filter fabric at room temperature to remove the formed salts from the reaction mixture, and then, was filtered through a filter fabric at a temperature of −2° C. to remove the unreacted alcohol from the resultant reaction mixture. Thus, polyoxypropylene (20)-2-hexadecyl-octadecyl alcohol ether having the following properties was obtained.

| Viscosity (at 210° F.) | 19.9 centistokes (cst) |
|---|---|
| Hydroxyl Number | 35.6 |
| Average Molecular Weight | 1576 |
| pH | 6.6 |
| Turbidity Point | 0 to 2° C. |
| Freezing Point | −10° C. to −12° C. |
| Propylene Oxide Addition Molar Number | 18.0 |
| H.L.B. Value | 5.5 |

1 mol of the polyoxypropylene (20)-2-hexadecyloctadecyl alcohol ether and, as a catalyst, 0.3% by weight of potassium hydroxide based upon the alcohol ether were charged into an autoclave, and then, after air present in the autoclave was replaced with dry nitrogen, the mixture was heated to a temperature of 140° through 160° C. under agitation to completely dissolve the catalyst. Then, 25 mol of ethylene oxide was dropwise added from a cooled dropping apparatus provided with a cooling means to the mixture in the autoclave and the mixture was stirred the same conditions. The agitation was continued for further 35 minutes to age the reaction mixture after the completion of the reaction.

The reaction mixture was taken out of the autoclave after cooling and was treated in a similar manner to that mentioned above in the preparation of the polyoxypropylene (20)-2-hexadecyl-octadecyl alcohol ether. The formed salts which were still hot were filtered off through a filter fabric to produce a product. The reaction product could be optionally washed with a methanol-hexane mixture to remove the unreacted propylene oxide addition product. The polyoxyethylene (25) polyoxpropylene (20)-2-hexadecyl-octadecyl alcohol having the following properties was obtained.

| Viscosity (at 210° F.) | 396 cst |
|---|---|
| Hydroxyl Number | 15.0 |
| Average Molecular Weight | 2728 |
| pH | 5.7 |
| Freezing Point | 42° C. |
| Propylene Oxide Addition Molar Number | 26.0 |
| H.L.B. Value | 10.5 |

EXAMPLE 2

Synthesis of polyoxyethylene (25) polyoxypropylene (5)-2-eicosyl-docosyl alcohol ether.

Into an autoclave 1 mol 2-eicosyl-docosanol and, as a catalyst, 0.3% by weight of potassium hydroxide based upon the 2-eicosyl-docosanol were charged, and then, the mixture was reacted and treated in the manner described in Example 1, except that 5 mol of propylene oxide was used in lieu of 20 mol of propylene oxide. Polyoxypropylene (5)-2-eicosyl-docosyl alcohol ether having the following properties was obtained.

| Viscosity (at 210° F.) | 18.0 cst |
|---|---|
| Hydroxyl Number | 47.9 |
| Average Molecular Weight | 900 |
| pH | 6.2 |
| Turbidity Point | 2° C. |
| Freezing Point | −10° C. |
| Propylene Oxide Addition Molar Number | 5.8 |

| H.L.B. Value | 2.8 |

From the polyoxypropylene (5)-2-eicosyl-docosyl alcohol ether thus obtained polyoxyethylene (25) polyoxypropylene (5)-2-eicosyl-docosyl alcohol ether was produced by the addition reaction of 25 mol of ethylene oxide in the same manner as described in Example 1. Since the starting alcohol material had a larger molecular weight than that of Example 1 and since the amounts of the unreacted propylene oxide addition product as well as the unreacted ethylene oxide addition product were larger than those of Example 1, the reaction product was washed with a methanol-hexane mixture. The polyoxyethylene (25) polyoxypropylene (5)-2-eicosyl-docosyl alcohol ether having the following properties was obtained.

| Viscosity (at 210° F.) | 348 cst |
| Hydroxyl Number | 20.2 |
| Average Molecular Weight | 2022 |
| pH | 6.0 |
| Freezing Point | 40° C. |
| Propylene Oxide Addition Molar Number | 25.5 |
| H.L.B. Value | 10.4 |

EXAMPLE 3

Solubilization Text of Perfume into Aqueous Alcohol Solution.

1% by weight of floral perfume having a H.L.B. value of 5.0 was solubilized into 55% by weight of an aqueous ethanol solution by using, as a solubilizing agent, polyoxyethylene (25) polyoxypropylene (20)-2-hexadecyl-octadecyl alcohol ether under the following formulation.

| | % by weight |
| --- | --- |
| (a) Distilled Water | 43.8 |
| (b) Ethyl alcohol | 55 |
| (c) Perfume | 1 |
| (d) Polyoxyethylene (25) polyoxypropylene (20)-2-hexadecyl-octadecyl alcohol ether | 0.2 |

The solution of the components (c) and (d) uniformly dissolved in the component (b) was added, with stirring, into the component (a) at room temperature. This solubilized system was stable for two months in a constant temperature bath which was controlled to a cycle temperature of 5 through 50° C. This stability was not changed when 0.1% by weight of citric acid was incorporated into the solubilized system or when 0.1% by weight of sodium hydroxide was incorporated into the solubilized system.

EXAMPLE 4

Solubilization Test of Perfume into Aqueous Alcohol Solution.

1% by weight of the perfume used in Example 3 was solubilized into 35% by weight of an aqueous isopropanol solution by using the solubilizing agent of Example 3 under the following formulation.

| | % by weight |
| --- | --- |
| (a) Distilled Water | 63.8 |
| (b) Isopropanol | 35 |
| (c) Perfume of Example 3 | 1 |
| (d) Solubilizing Agent of Example 3 | 0.2 |

The solution of the components (c) and (d) uniformly dissolved in the component (b) was added, with stirring, into the component (a) at room temperature. This solubilized system was stable for two months in a constant temperature bath, which was controlled to a cycle temperature of 5 through 50° C., under neutral, weak acidic and weak alkaline conditions.

COMPARATIVE EXAMPLE 1

Solubilization Test of Perfume into Aqueous Alcohol Solution.

In order to evaluate the solubilization effect of the present compound 1% by weight of the perfume of Example 3 was solubilized into 55% by weight of an aqueous ethanol solution and 35% by weight of an aqueous isopropanol solution by using 0.2% by weight of polyoxyethylene (30) hardened castor oil ether, which is known as a solubilizing agent having the most solubilization capacity in a high concentration aqueous solution of a lower alcohol among the available solubilizing agents on the market.

There were not apparent difference between the stability of these solubilizing systems and the systems of Examples 3 and 4 under a neutral region. However, turbidity was observed in both ethanol and isopropanol systems under a weak acidic condition and two months later, precipitates were formed. Thus, the solubilizing agent of this invention has outstanding solubilizing characteristics, especially in a weak acidic region, compared to the known solubilizing agent, polyoxyethylene (30) hardened caster oil which is known as an effective solubilizing agent.

EXAMPLE 5

Solubilizing Test of Vitamin E Acetate into Aqueous Alcohol Solution.

1% of weight of vitamin E acetate having a H.L.B. value of 2.6 was solubilized into 55% by weight of an aqueous ethanol solution by using, as a solubilizing agent, polyoxyethylene (25) polyoxypropylene (5)-2-eicosyl-docosyl alcohol ether under the following formulation.

| | % by weight |
| --- | --- |
| (a) Distilled Water | 43.8 |
| (b) Ethyl alcohol | 55 |
| (c) Vitamin E acetate | 1 |
| (d) Polyoxyethylene (25) polyoxypropylene (5)-2-eicosyl-docosyl alcohol ether | 0.2 |

The solution of the components (c) and (c) uniformly dissolved in the component (b) was added, with stirring, into the component (a) at room temperature. This solubilized system was stable, as in Example 3, for two months in a constant temperature bath, which was controlled to a cycle temperature of 5° through 50° C., under neutral, weak acidic and weak alkaline conditions.

EXAMPLE 6

Solubilization Test of Vitamin E Acetate into Aqueous Alcohol Solution.

1% by weight of the vitamin E acetate of Example 5 was solubilized into 35% by weight of an aqueous isopropanol solution by using the solubilizing agent of Example 5 under the following formulation.

|  | % by weight |
|---|---|
| (a) Distilled Water | 63.8 |
| (b) Isopropanol | 35 |
| (c) Vitamin E acetate of Example 5 | 1 |
| (d) Solubilizing Agent of Example 5 | 0.2 |

The solution of the components (c) and (d) uniformly dissolved in the component (b) was added, with stirring, into the component (a) at a room temperature. This solubilized system was stable, as in Example 5, for two months in a constant temperature bath, which was controlled to a cyclic temperature of 5° through thrugh 50° C., under neutral, weak acidic and weak alkaline conditions.

EXAMPLE 7

Solubilization Test of capric acid triglyceride into Aqueous Alcoholic Solution.

1% by weight of capric acid triglyceride having a H.L.B. value of 2.7 was solubilized into 55% by weight of an aqueous ethanol solution by using, as a solubilizing agent, polyoxyethylene (25) polyoxypropylene (10)-2-eicosyl-docosyl alcohol ether under the following formulation.

|  | % by weight |
|---|---|
| (a) Distilled Water | 43.8 |
| (b) Exthyl alcohol | 55 |
| (c) Capric acid triglyceride | 1 |
| (d) Polyoxyethylene (25) polyoxypropylene (10)-2-eicosyl-docosyl alcohol ether | 0.2 |

The solution of the components (c) and (d) uniformly dissolved in the component (b) was added, with stirring, into the component (a) at room temperature. This solubilized system was stable, as in Example 3, for two months in a constant temperature bath, which was controlled to a cyclic temperature of 5° through 50° C., under neutral, weak acidic and weak alkaline conditions.

Comparative Example 2

Solubilization Tests of Vitamin E Acetate and Capric Acid Triglyceride into Aqueous Alcoholic Solution.

In order to evaluate the solubilizing effect of the present compound, 1% by weight of Vitamin E acetate of Example 5 and 1% by weight of capric acid triglyceride of Example 7 were solubilized into 55% by weight of an aqueous ethanol solution by using 0.2% by weight of polyoxyethylene (30) hardened castor oil ether, which is known as an effective solubilizing agent, in the manner as described in Examples 5 and 7, respectively. The turbidity was observed in both solubilizing systems containing polyoxyethylene (30) hardened castor oil ether at a pH of 6. Thus, the solubilizing agent of the present invention has superior solubilizing characteristics with respect to substances which are to be solubilized and which have a low H.L.B. value, compared to the known effective solubilizng solubilizing (i.e., polyoxyethylene (30) hardened caster oil ether).

As will be clear from the above-mentioned descriptions, as well as Examples and the Comparative Examples, the solubilizing agent of the present invention has the following novel and progressive advantages.

(1) The present solubilizing agent has an outstanding solubilizing capacity in an high concentration solution of a lower alcohol in water.

(2) The H.L.B. value of the lyophillic moiety of the present solubilizing agent can be freely adjusted to a H.L.B. value of the substance to be solubilized.

(3) The stability under acid resistant and alkaline resistant conditions is good.

(4) Since a higher saturated and branched primary alcohol is used, good oxidative stability is obtained and susceptibility to discoloration and deterioration is small.

(5) Since the amount of the unreacted product of primary alcohol can be minimized by the addition reaction of propylene oxide being carried out prior to the addition reaction of ethylene oxide, the purification and separation operation of the present solubilizing agent is easy.

EXAMPLE 8

A liquid hair preparation (hair tonic) containing a high concentration solution of a lower alcohol in water was prepared by the following formulation.

|  | % by weight |
|---|---|
| (a) Ethyl alcohol | 55.0 |
| (b) Lanolin derivative | 2.0 |
| (c) Perfume | 1.0 |
| (d) Polyoxyethylene (25) polyoxypropylene (20)-2-hexadecyl-octadecyl alcohol ether | 1.0 |
| (e) Salicylic acid | 0.2 |
| (f) Vitamin $B_6$ | 0.2 |
| (g) Ultraviolet absorbing agent (2-hydroxy-4-metoxybenzophenone) | 0.1 |
| (h) Coloring agent | 0.0005 |
| (i) Demineralized water | 40.0 |

The components (b) through (h) were dissolved into the component (a) and, then, this solution was added with stirring to the component (i) at room temperature. Then, this mixture was filtered. Thus, a transparent liquid hair preparation was prepared.

EXAMPLE 9

An aftershave lotion containing a high concentration solution of a lower alcohol in water was prepared by the following formulation.

|  | % by weight |
|---|---|
| (a) Ethyl alcohol | 50.0 |
| (b) Glycerine | 2.0 |
| (c) Perfume | 1.0 |
| (d) Carbowax | 1.0 |
| (e) Polyoxyethylene (25) polyoxypropylene (10)-2-eicosyl-dococyl alcohol ether | 0.8 |
| (f) Ultraviolet absorbing agent (2-hydroxy-4-methoxybenzophenone) | 0.1 |
| (g) Coloring agent | 0.0005 |
| (h) Allantoin | 0.1 |
| (i) Demineralized water | 45.0 |

The components (b) through (g) were dissolved into the component (a), and then, this clear solution was added with stirring to a mix of the components (h) and (i) at room temperature. The mixture was sufficiently agitated and then filtered. Thus, an aftershave lotion was prepared.

What we claim is:

1. A polyoxypropylene polyoxyethylene addition ether of a higher branched primary saturated alcohol having the general formula (I),

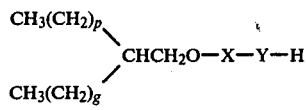 (I)

wherein p represents an integer of 7 to 19, q represents an integer of p plus two, X represents

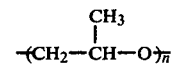

(wherein n represents an integer of 5 to 30) and Y represents $-(CH_2\text{-}CH_2\text{-}O)_m$ (wherein m represents an integer of 5 to 60).

2. A polyoxypropylene polyoxyethylene addition ether as claimed in claim 1, wherein the total molecular weight of the higher branched alcohol moiety and the polypropylene oxide moiety is not less than 900.

3. A polyoxypropylene polyoxyethylene addition ether as claimed in claim 1, wherein said addition ether is polyoxyethylene (25) polyoxypropylene (20)-2-hexadocyl-octadecyl alcohol ether.

4. A polyoxypropylene polyoxyethylene addition ether as claimed in claim 1, wherein said addition ether is polyoxyethylene (25) polyoxypropylene (5)-2-eicosyl-docosyl alcohol ether.

* * * * *

UNITED STATES PATENT OFFICE
CERTIFICATE OF CORRECTION

Patent No. 4,171,455    Dated October 16, 1979

Inventor(s) Kenichi Tomita, et al

It is certified that error appears in the above-identified patent and that said Letters Patent are hereby corrected as shown below:

Column 3, line 1: "fromm" should be --from--.

Column 4, line 63: "fur" should be --for--.

Column 6, line 37: "polyoxpropylene" should be --polyoxypropylene--.

Column 8, line 61: "(c)" (2nd occurrence) should be --(d)--.

Column 1, line 22; Column 4, lines 21, 27, 47, 50; Column 8, line 39; Column 9, lines 60, 64; and Column 10, line 2: change "caster" to --castor--.

Signed and Sealed this

Eighth Day of July 1980

[SEAL]

Attest:

SIDNEY A. DIAMOND

Attesting Officer   Commissioner of Patents and Trademarks